United States Patent [19]
Huebner et al.

[11] Patent Number: 5,182,366
[45] Date of Patent: Jan. 26, 1993

[54] CONTROLLED SYNTHESIS OF PEPTIDE MIXTURES USING MIXED RESINS

[76] Inventors: Verena D. Huebner, 512 Zinnia Ct., Benicia, Calif. 94510; Daniel V. Santi, 211 Belgrave Ave., San Francisco, Calif. 94117

[21] Appl. No.: 523,791

[22] Filed: May 15, 1990

[51] Int. Cl.$^5$ ............................ C07K 1/00; C07K 1/04
[52] U.S. Cl. ....................................... 530/334; 530/333
[58] Field of Search ....................... 530/334, 300, 333; 514/2

[56] References Cited

U.S. PATENT DOCUMENTS

| 5,010,175 | 4/1991 | Rutter et al. | 530/334 |
| 5,053,454 | 10/1991 | Judd | 530/334 |

FOREIGN PATENT DOCUMENTS

WO86/00991 2/1986 PCT Int'l Appl. ................. 530/334
WO86/06487 11/1986 PCT Int'l Appl.
WO89/04325 5/1989 PCT Int'l Appl.

OTHER PUBLICATIONS

Houghten, R., *Proc. Natl. Acad. Sci.*, 82:5131–5135, 1985.
Houghten, R. et al., *Biotechniques*, 4(6):522–524, 1986.
Genson, H. et al., *Proc. Natl. Acad. Sci.*, 81: 3998–4002, 1984.

*Primary Examiner*—Lester L. Lee
*Assistant Examiner*—Susan M. Perkins
*Attorney, Agent, or Firm*—Morrison & Foerster; Karl Bozicevic

[57] ABSTRACT

A method of preparing a mixture of peptides having a known composition and containing a peptide of a desired amino acid sequence is disclosed. The method involves three essential steps. First a given amount of a mixture of amino acyl or peptide derivatized resin is divided into a number of pools with each pool containing an equal molar amount of the resin mixture. Second a different single amino acid is coupled to the resin mixture in each of the pools and the coupling reaction is driven to completion. The peptide mixtures in each of the pools are then mixed together to obtain a complex peptide mixture containing each peptide in retrievable and analyzable amounts. The steps can be repeated to lengthen the peptide chains and methods can be employed to retrieve the desired peptide from the mixture and carry out analyses such as the determination of the amino acid sequence.

25 Claims, 2 Drawing Sheets

CONTROLLED SYNTHESIS OF PEPTIDE MIXTURES USING MIXED RESINS

FIELD OF THE INVENTION

The invention relates to methods of synthesis to obtain desired mixtures of peptides and obtaining therefrom peptides having specific sequences. More particularly, it concerns a method to obtain defined peptide mixtures, which mixture will include desired peptides and then selecting those desired peptides which have high affinities for a given receptor (or other desired property) and identifying and analyzing desired peptides of these mixtures.

BACKGROUND OF THE INVENTION

In order to synthesize a single defined peptide sequence those skilled in the art generally use the Merrifield method to "grow" peptide chains attached to solid supports. The process of synthesizing these individual peptides has been automated. Commercially available equipment can be used to synthesize peptides of twenty or more amino acids in length. To obtain peptides of arbitrary length, the resulting peptides can be ligated with each other by using appropriate protective groups on the side chains and by employing techniques permitting the removal of the synthesized peptides from the solid supports without deprotecting them. Thus, the synthesis of individual peptides of arbitrary length is known in the art.

Although the synthesis of a particular peptide may be routine, it is necessarily laborious. This presents a large practical problem in a situation where it is not previously known which of a multiplicity of peptides is, in fact, the preparation desired. While it is theoretically possible to synthesize all possible candidates and test them with whatever assay is relevant (immunoreactivity with a specific antibody, interaction with a specific receptor, particular biological activity, etc.), to do so using the foregoing method would be comparable to the generation of the proverbial Shakespeare play by the infinite number of monkeys with their infinite number of typewriters. In general, the search for suitable peptides for a particular purpose has been conducted only in cases where there is some prior knowledge of the most probable successful sequence. Therefore, methods to systematize the synthesis of a multiplicity of peptides for testing in assay systems would have great benefits in efficiency and economy, and permit extrapolation to cases where nothing is known about the desired sequence.

Two such methods have so far been disclosed. One of them, that of Houghten, R.A., *Proc Natl Acad Sci USA* (1985) 82:5131–5135, is a modification of the above Merrifield method using individual polyethylene bags. In the general Merrifield method, the C-terminal amino acid of the desired peptide is attached to a solid support, and the peptide chain is formed by sequentially adding amino acid residues, thus extending the chain to the N-terminus. The additions are carried out in sequential steps involving deprotection, attachment of the next amino acid residue in protected form, deprotection of the peptide, attachment of the next protected residue, and so forth.

In the Houghten method, individual polyethylene bags containing C-terminal amino acids bound to solid support can be mixed and matched through the sequential attachment procedures so that, for example, twenty bags containing different C-terminal residues attached to the support can be simultaneously deprotected and treated with the same protected amino acid residue to be next attached, and then recovered and treated uniformly or differently, as desired. The resultant of this is a series of polyethylene bags each containing a different peptide sequence. Although each bag will contain many peptides, all of the peptides in any one bag are the same. The peptides in each bag can then be recovered and individually biologically tested.

An alternative method has been devised by Geysen, H.M., et al, *Proc Natl Acad Sci USA* (1984) 81:3998–4002. See also W086/06487 and W086/00991. This method is a modification of the Merrifield system wherein the C-terminal amino acid residues are bound to solid supports in the form of polyethylene pins and the pins treated individually or collectively in sequence to attach the remaining amino acid residues. Without removing the peptides from support, these peptides can then efficiently be effectively individually assessed for the desired activity, in the case of the Geysen work, interaction with a given antibody. The Geysen procedure results in considerable gains in efficiency of both the synthesis and testing procedures, while nevertheless producing individual different peptides. It is workable, however, only in instances where the assay can be practically conducted on the pin-type supports used. If solution assay methods are required, the Geysen approach would be impractical.

The present invention offers an alternative to the above described methods by utilizing synthesis of mixtures containing large numbers of different peptides as well as providing a means to isolate and analyze those members or families of members of the mixture which have a desired property.

SUMMARY OF THE INVENTION

The method of the invention involves splitting a mixture of resins derivatized with different amino acids or peptides into equal pools, coupling a single amino acid to each of the pools, and recombining each of the pools of newly synthesized peptide resins in the individual pools to obtain a mixture of known composition. The steps are repeated to increase the size of the peptides and the number of different peptides in the mixture.

A primary object of the invention is to provide a method of making a mixture of peptides which mixture has a known composition and contains a plurality of different peptides (usually including a desired peptide with a target property) wherein each of the different peptides is present in an amount sufficient for retrieval and analysis.

An advantage of the invention is that the coupling reactions in the individual pools can be driven to completion by adjusting reaction conditions and adding large excesses of each of the amino acids added to the pools.

A feature of the invention is that the coupling reactions of any of the pools can be monitored by an analytical means to determine the degree of completion of the reaction.

Another advantage of the invention is that it allows for the optimization of the specific activation chemistry of each of the amino acids used.

Another feature of the invention is that it allows for corrections in sequence dependent difficulties in coupling by double coupling and changing coupling conditions (activation chemistry, solvents, etc.)

Another object of the invention is to provide a method which allows for a specific synthetic protocol for producing a composition which comprises a complex mixture of peptides (the composition of the mixture being known based on the protocol) thus eliminating the need for characterization of the mixture after synthesis.

Yet another object of the present invention is to provide a method for producing a mixture of peptides which mixture will include a peptide having a desired target property.

An advantage of the present invention is that mixtures produced by the invention will have peptides having the desired target property which peptides can be retrieved and analyzed.

Another feature of the present invention is that each of the peptides in the mixture of peptides (having a given amino acid sequence and being produced according to the disclosed process) are each present in retrievable and analyzable amounts.

An advantage of the present invention is that it allows for the production of an extremely large number of different peptides in a peptide mixture which mixture of peptides can then be screened for the presence of peptides having a particular target property.

Another advantage of the present invention is that extremely large numbers of peptides can be produced utilizing a relatively few number of different processing steps.

These and other objects, advantages and features of the present invention will become apparent to those persons skilled in the art upon reading the details of the synthesis and usage as more fully set forth below. Reference being made to the accompanying figures forming a part hereof.

BRIEF DESCRIPTION OF THE DRAWINGS

The invention may be better understood and its numerous objects, advantages and features will become apparent to those skilled in the art by reference to the accompanying figures as follows.

DETAILED DESCRIPTION OF THE PREFERRED EMBODIMENTS

Figure 1:
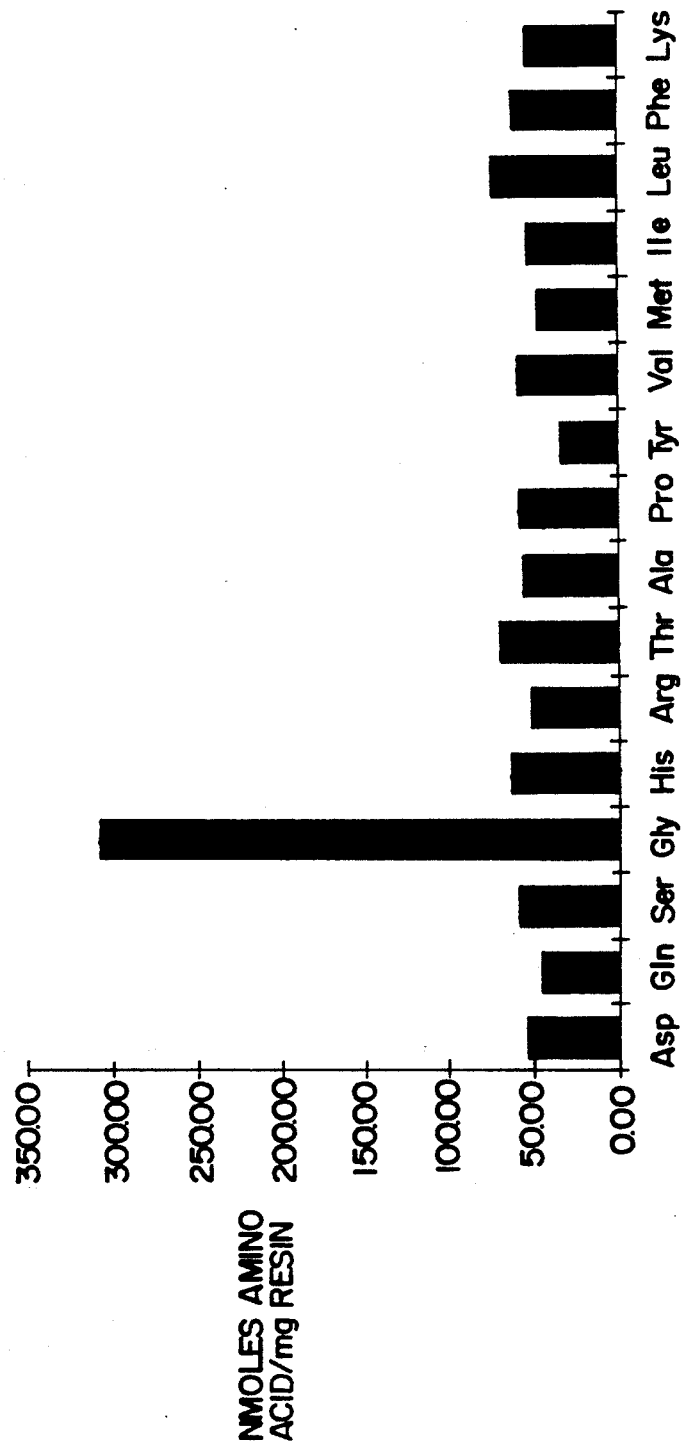
FIG. 1 is a graph showing the amino acid composition of a peptide mixture prepared in accordance with the present invention.

Before the present method of making a mixture of peptides and process for determining the composition of a complex mixture of peptides are described, it is to be understood that this invention is not limited to the particular amino acids, resins, peptides or processes described as such reactants and processes may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a peptide" includes a large number of peptides of the same sequence and reference to "the process" or "the step" includes alternative processes and steps of the general type described herein and so forth.

Definitions

As used in connection with the present mean a invention, the term "amino acyl resin" shall mixture of acceptor amino acids which has its N-terminus deprotected but which has a protected C-terminus. Further, the term "peptide derivatized resin" shall mean a mixture of acceptor peptides wherein the N-terminal amino acid has been deprotected and wherein the C-terminus of the peptide is protected. Accordingly, such "amino acyl resins" or "peptide derivatized resins" are generally classified as being "acceptors" meaning that additional amino acids can be added at the N-terminus. Further, unless described as a "single" compound, disclosed compositions are mixtures of peptides or resins i.e. heterogeneous groups of compounds produced from single compounds by polymerization. The heterogeneous group or mixture will contain a statistical mixture of compounds i.e., a range of different compounds over a range of proportional amounts.

The term "activated amino acid" shall mean an amino acid which is supplied to an amino acyl resin or peptide derivatized resin under conditions such that the carboxyl but not the amino group is available for bond formation with the acceptor resin. Accordingly, terms such as "acceptor" and "resin" apply to the deprotection of the N-terminus of the amino acid whereas terms such as "amino acid" and "activated amino acid" refer to the status of the carboxyl group of the amino acid as compared with its amino group and indicate that such amino acids will react with and form a peptide bond with the amino group of the resin.

With respect to the peptide mixtures specifically described in this disclosure, it should be pointed out that Fmoc chemistry was used with the amino acids coupled as active pentafluorophenyl esters (OPfp esters). However, it will be apparent to those skilled in the art that methods of the present invention can be carried out using other N-alpha protecting chemistries (such as Boc) or other carboxyl terminal activation methods (such as HoBt esters, symmetric anhydrides, etc.).

"Target" characteristic or property refers to that desired to be exhibited by the peptide or family, such as specific binding characteristics, contractile activity, behavior as a substrate, activity as a gene regulator, etc.

The method is similarly applied to solution phase synthesis, wherein the acceptor peptides or amino acids are supplied as a mixture for reaction with an appropriate mixture of activated amino acids. Either or both mixtures are concentration-adjusted to account for rate constant differentials.

MODES OF CARRYING OUT THE INVENTION

A method of preparing a mixture of peptides (with different amino acid sequences) having a known composition and containing a peptide of a desired amino acid sequence is disclosed. The method involves three essential steps as follows:

(1) a given amount of a mixture of amino acyl or peptide-derivatized resins are divided into a number of pools (or subamounts) with each pool (or subamount) containing an approximately equal molar amount of each resin;

(2) a different single activated amino acid is coupled to each resin in each of the pools (or subamounts) created in step (1) and the coupling reaction is driven to completion; and (3) equal molar amounts of the peptides in each of the pools (or subamounts) obtained in step (2) are then mixed together to obtain a peptide mixture of known composition (i.e., containing substantially equal molar amounts of each of the peptides).

Two important points should be made, (a) if any amino acid residue in the peptide to be produced is known then all of the activated amino acids added to each pool in that step, e.g., step (2) will be the same; and (b) the steps (1-3) can be repeated any number of times to lengthen the peptide chain.

Approximately equimolar amounts of amino acids and mixtures can be used as acceptors independently with respect to the next activated amino acyl addition to create lengthened peptide acceptors which can be remixed and divided. Thus, the number of reactions which must be independently conducted is limited to the number of residues which are alternatives at a single position times the number of residues in the chain, even though the number of peptides ultimately synthesized is quite large. Thus, for example, to synthesize a pentamer with 10 alternatives for each position, only 50 independent reactions are required to synthesize a mixture containing $10^5$ peptides. In that the method produces each of the $10^5$ peptides (each with a different sequence) in retrievable and analyzable amounts (preferably equal molar amounts) the method is an extremely powerful tool for obtaining a large group of peptides which can be screened for a desired peptide.

Methods can be employed to retrieve the desired peptide from the mixture and carry out analyses such as the determination of the amino acid sequence by methods known to those skilled in the art. In step (2) sufficient amounts of activated amino acid are added so as to produce enough of the peptide in each pool so that when the pools are combined in step (3) each of the peptides in the resulting mixture will be present in that mixture in retrievable and analyzable amounts.

The invention permits a practical synthesis of a mixture of a multitude of peptide sequences, in predictable or defined amounts, (within statistically acceptable variation) for the intended purpose. In addition, the invention permits this mixture to be selected for the desired peptide members, individually or as groups and the determination of sequences of these selected peptides so that they can be individually synthesized in large amounts if desired. Because mixtures of many peptides are used, prejudicial assumptions about the nature of the sequences required for the target biological activity is circumvented. However, if information about a peptide is known such as the amino acid residue at a given position in the chain, that information can be readily made use of in the method of the invention.

Thus, in one aspect, the invention is directed to a method to synthesize a mixture of peptides of defined composition. The relative amount of each peptide in the mixture can be controlled by changing the relative amount of each peptide pool in step (2) which is added in step (3), and, if desired, by changing mixtures of starting resins with C-terminal amino acids or peptides conjugated to them.

It should be noted that while the invention method of synthesis is most usually and practically conducted using solid-supported peptides, there is no reason it cannot be employed for solution phase synthesis, wherein the acceptor amino acid or peptide is simply blocked at the carboxyl terminus.

In another aspect, the invention is directed to a method to select those components (individually or as families) of the mixture which have the desired "target" activity. Sequence information on these peptides can also be obtained. Thus, the invention is also directed to a method to separate the desired peptide, or peptide family, from the original composition; this comprises effecting differential behavior under conditions which result in physical separation of components, such as binding to a selective moiety, differential behavior with respect to solubility, shape or transport, or modification of the structure of selected peptides or mixtures by a reagent or enzyme which converts only the desired peptides to a form that can be conveniently analyzed or separated.

Finally, the invention is directed to the combination of the foregoing with methods to analyze peptide sequences, often while these sequences are still present in mixtures.

In addition to the foregoing aspects, various additional combinations thereof are useful.

Producing and Retrieving a Desired Peptide

In general, the goal of the invention is to provide a means to obtain and identify one or a family of specific peptide sequences which have a target utility such as ability to bind a specific receptor or enzyme, immunoreactivity with a particular antibody, and so forth. To achieve this end, the invention most preferably involves the three following aspects:

(a) Preparation of a mixture of many peptides putatively containing the desired sequences;

(b) Retrieval or selection from the mixture of a particular subpopulation which has the desired characteristics; and (c) Analysis of the selected subpopulation to determine the peptide's amino acid sequence so that the desired peptide(s) can be synthesized alone and in quantity.

The essence of the invention is in the preparation (a) which is carried out in steps (1)-(3) referred to above. Unless a mixture is produced containing retrievable amounts of each of the different peptides no peptide could be retrieved and without the retrieval, as stated above in (b), no analysis, as stated above in (c), can be carried out.

Of course, repeated iterations of (a)-(c) using smaller and smaller populations can also be conducted.

Since a complex mixture of peptides is to be synthesized as the starting material for selection, no preconceived ideas of what the nature of the peptide sequence might be is required. This is not to imply that the method is inapplicable when preliminary assumptions can reasonably be made. In fact, the ability to make valid assumptions about the nature of the desired sequence makes it easier to carry out the methods of the invention. However, the advantages of the present invention over the prior art are further emphasized the less that is known about the desired protein.

Using for illustration only the twenty amino acids encoded by genes, a mixture in which each position of the peptide is independently one of these amino acids will contain 400 members if the peptide is a dipeptide; 8,000 members if it is a tripeptide; 160,000, if it is a tetrapeptide; 3,200,000 if there are five amino acids in the sequence; and 64,000,000 if there are six. Since alternative forms can be included, such as D amino acids, and noncoded amino acids, the number of possibilities is, in fact, dramatically greater.

The mixtures, in order to be subjected to procedures for selection and analysis of the desired members, must provide enough of each member to permit this selection and analysis. Using the current requirement, imposed by limitations of available selection and analysis techniques, about 100 picomoles of a peptide are needed in order to select the peptide and analyze its structure. The total amount of protein mixture required to get 100 picomoles of each peptide can be calculated, assuming that each of the peptides are present in equal amounts. The results of this calculation for peptides containing amino acids selected only from those naturally encoded by a gene are shown in Table 1 below.

The amount of the peptide added from each pool created in step (2) in order to make the mixture in step (3) must be controlled so that the component peptides in the mixture are present in approximately equal molar, or at least predictable., amounts. If this is achieved, then quantitation of the peptides selected by a protein receptor, or other method, will reflect the dissociation constants of the protein-peptide complexes. If the components of the mixture differ greatly, the amount of selected peptide will also reflect the concentration of that peptide in the mixture. Since it will not be feasible to quantitate the individual amounts of the components of very large mixtures of peptides, it is imperative that the amount of each peptide in the final mixture be closely measured and controlled by determining that each reaction in step (2) is driven to completion and each amount of peptide taken from the pools of step (2) and combined in step (3) is equal—that is equal molar so that the resulting mixture includes equal molar amounts of each peptide.

TABLE 1

| n | Number of Peptides | Mass of Mixture |
|---|---|---|
| 2 | 400 | 0.0022 mg |
| 3 | 8,000 | 0.44 mg |
| 4 | 160,000 | 8.8 mg |
| 5 | 3,200,000 | 176 mg |
| 6 | 64,000,000 | 3.5 g |

As shown in the table, even for a peptide of 6 amino acids wherein the mixture contains 64,000,000 separate components, only about 3.5 g of total mixture is required in order for the mixture to include retrievable and analyzable amounts of each peptide. Since most epitopes for immunoreactivity are often no greater than this length, and receptor binding sites are regions of peptides which may be of similar length, it would be feasible, even at current levels of sensitivity in selection and analysis, to provide a complete random mixture of candidate peptides, without presupposition or "second guessing" the desired sequence. This is further aided if peptides with staggered regions of variable residues and residues common to all components of the mixture can be used, as outlined below.

While the most frequent application of the invention is to discern an individual or small subgroup of amino acid sequences having a desired activity, in some instances it may be desirable simply to provide the mixture per se. Instances in which this type of mixture is useful include those wherein several peptides may have a cooperative effect, and in the construction of affinity columns for purification of several components. The method may also be used to provide a mixture of a limited number of peptides, which can then be separated into the individual components, offering a method of synthesis of large numbers of individual peptides which is more efficient than that provided by individual synthesis of these peptides.

Synthesis of Mixtures of Defined Composition

A general protocol for carrying out the invention and synthesizing a mixture of peptides will now be described. A container including a mixture of peptide resin is (1) split into equal parts or fractions, a different activated amino acid is (2) coupled to each of the resin fractions, the reaction in each fraction is monitored to ascertain that it has gone to completion, and the fractions are (3) recombined to form the mixture of peptides which mixture will contain each peptide (i.e., all amino acid sequence combinations) in retrievable and analyzable amounts.

Applying the above generalized protocol a description can be given wherein a mix is produced with any given number of carboxyl terminal amino acids present in a mix. This is done by preparing equimolar mixtures of amino-acyl resins by mixing the proper weights of resins based on their amino acid substitution (meq amino acid/g resin). Mixing can be carried out as a dilute slurry in Dimethylformamide (DMF), with vigorous mixing. The equimolarity of the resin mixture can be confirmed by amino acid analysis. For example, Fmoc chemistry can be used with amino acids coupled as active pentafluorophenyl esters (OPFp esters). Other N-$\alpha$ protecting chemistries (such as Boc), or other carboxyl terminal activation methods (such as HoBt esters, symmetric anhydrides, etc.) can be used.

The resin mixture can be split into equal portions, either by weight, or volumetrically, as a consistent slurry. It is important that the slurry be uniformly consistent to insure that each portion of the mixture contains an equal molar amount of peptide resin. The peptide mixtures to be divided can be synthesized manually. However, mixtures of peptides with a combination of constant and variable residues can be made using a combination of automated and manual approaches. Further, a sequence of constant residues can be added on an automated synthesizer. When using an automated synthesizer resin being produced can be removed at different points during synthesis to obtain a desired mixture. Any mixture produced via automation can then be split into equal portions and the mixed amino acids coupled manually.

EXAMPLES

The following examples are provided so as to provide those of ordinary skill in the art with a complete disclosure and description of how to make the peptide mixtures of the invention and are not intended to limit the scope of what the inventors regard as their invention. Efforts have been made to insure accuracy with respect to numbers used (e.g., amounts, temperature, etc.) but some experimental errors and deviation should be accounted for. Unless indicated otherwise, parts are parts by weight, temperature is in degrees C, and pressure is at or near atmospheric. It should also be noted that the examples put forth below are examples of the method of the present invention which are carried out manually. Such methods can be automated and techniques for automatically carrying out the steps of the invention will be apparent to those skilled in the art upon reading the method and step descriptions put forth below.

EXAMPLE 1

The synthesis of the following peptide mixture is described:

(NH$_2$)-mix1-Gly-mix2-mix3-(COOH)

mix1 = Arg, Ala, Val, Ser, Met
mix2 = Lys, Ile, Thr, Pro, Tyr
mix3 = Asp, His, Gln, Phe, Leu (mixture of hydroxymethyl amino acid-resins).

Mixing of Resins

Fifty μmoles of each of the 5 amino acid resins, Asp, His, Gln, Phe, and Leu were weighted out based on their substitution and mixed by making them a thin slurry in DMF (approx. 1g/40 ml) and shaking vigorously on a vortexer for 1 hr, followed by washing with methylene chloride (approx. 100 ml) and drying under vacuum. The resin mix was then separated equally into 5 reaction vessels (by weight).

Deprotection and Coupling

Resins in the mixture were deprotected by incubation with 20% piperidine in DMF (2×3 ml, for 10 min each), followed by extensive washing (3×3 ml of DMF, followed by 3×3 ml of methanol, and 3×3 ml DMF). To each reaction vessel was added 0.25 mmoles of activated amino acid.

For ease of synthesis, the activated amino acids were added as preformed pentafluorophenyl esters (OPfp esters), except for serine and threonine, which were added as the preformed 3-hydroxy-4-oxo-3,4-dihydrobenzotriazine esters (ODHBt esters). 0.2 ml of 0.5 M HOBt in DMF was added to each coupling reaction. The reactions were allowed to proceed for 2 hrs. Excess amino acid was aspirated away, and the resin washed with DMF (3×3 ml) followed by methanol 3×3 ml). The completeness of each of the coupling reactions was verified by qualitative ninhydrin (tradename for triketohydrine hydrate) which, if negative, indicates greater than 99% coupling (Kaiser, E., Colescott, R.L., Bossinger, C.D., and Cook, P.E., Anal Biochem (1970) 34:595 (1970)).

The resins obtained as a result of the reaction with the activated amino acids were recombined, swollen in DMF and mixed as described above. In cycles 2 and 4, which required mixtures, the resins were again split and treated as described above, with the appropriate amino acids coupled. At position 3, a single amino acid, glycine, was desired. The resins were combined and glycine was coupled to the entire resin in a single reaction.

Results

Characterization by amino acid analysis (Bidlingmeyer, B.A., Cohen, S.A., and Tarvin, T.L. *J Chromatogr* (1984) 336:93-104) of the final peptide product of the peptide mixture described above shows the peptide to have the amino acid composition shown in FIG. 1. It can be seen that all of the amino acids, with the exception of glycine, are present in essentially equimolar amounts, indicating that we have synthesized a substantially equimolar mixture of peptides. Glycine, as predicted from the theoretical composition of the peptide, is present in a 5 fold greater amount than the other amino acids. Tyrosine appears somewhat low, probably in some degree due to oxidation during hydrolysis. These results clearly demonstrate the suitability of the mixed resin approach for synthesizing equimolar mixtures of peptides.

EXAMPLE 2

Figure 2:
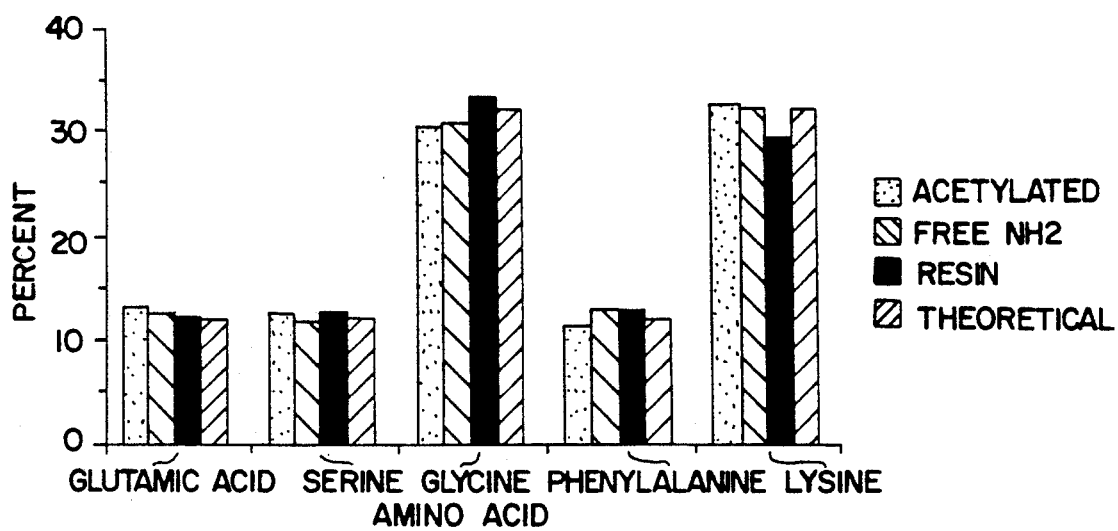
FIG. 2 is a graph showing the percent amount of certain amino acids in pools.
Figure 3:
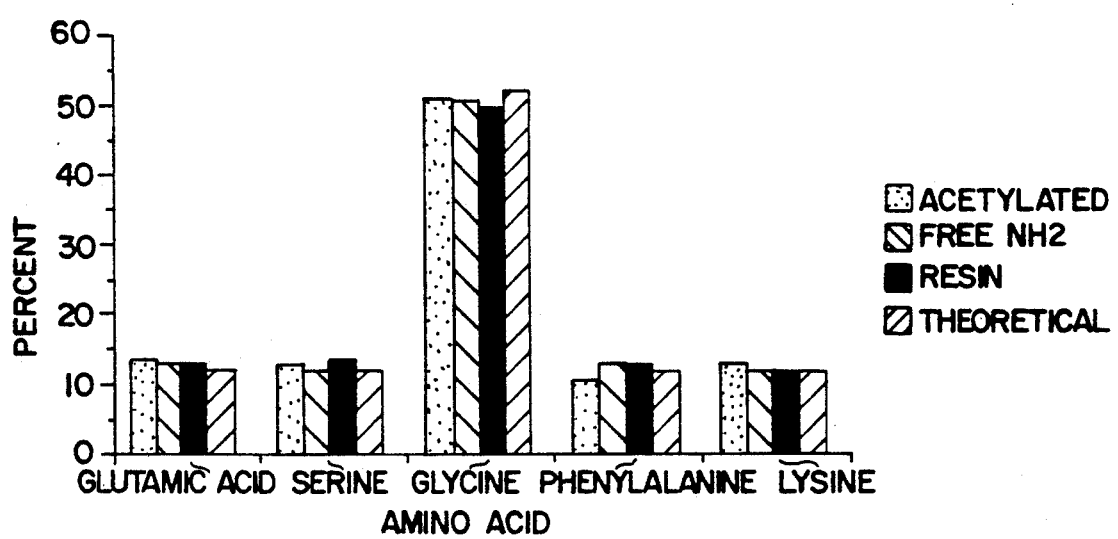
FIG. 3 is a graph showing the percent amount of certain amino acids in pools.

A second set of peptide mixtures was synthesized using the mixed resin method. In this case, all possible combinations of pentamers using the amino acid basis set of Gly, Lys, Glu, Phe, and Ser were synthesized. These were synthesized as 25 pools, each containing 125 different peptides. The synthesis was designed so that each pool contained the same amino terminal amino acids and equimolar mixes of all 5 amino acids at the other 3 residues (e.g., GG-mix-mix-mix, GK-mix-mix-mix, SF-mix-mix-mix, etc.). The synthesis was carried out using the methodology illustrated above. FIGS. 2 and 3 show the amino acid analysis results for 2 of the 25 pools. The theoretical values for each amino acid based on the expected composition of the pool are shown next to the values obtained. It can be seen that the actual amino acid composition of the pools agrees very closely with the theoretical, again demonstrating the feasibility of this method for the controlled synthesis of peptide mixtures.

For convenience in discussion, the description is limited to only a few amino acids. However, the invention is not thus limited. Alternate amino acid residues, or other acceptor chemical monomers such as hydroxyproline, α-aminoisobutyric acid, sarcosine, citrulline, cysteic acid, t-butylglycine, t-butylalanine, phenylglycine, cyclohexylalanine, β-alanine, 4-aminobutyric acid, and so forth can also be included in the peptide sequence in a completely analogous way. The D forms of the encoded amino acids and of alternate amino acids can, of course, also be employed. The manner of conducting syntheses, and of conducting selection and analysis is entirely analogous to that described above regardless of the amino acids used.

As a general proposition, it is not so simple to obtain mixtures of peptides having a defined composition, as might be supposed. Using the general Merrifield approach, one might assume that a mixture of twenty different derivatized resins, each derivatized with a different amino acid encoded by the gene, might be obtained in two different ways. Firstly, the mixture could be obtained using 20 times 20 or 400 different reaction vessels. Secondly, one might assume the mixture could be obtained by simultaneously reacting with a mixture containing the N-blocked, activated esters of the twenty amino acids. The random reaction of the activated amino acids with the derivatized resins would then, presumably, result in the 400 possible dipeptide combinations.

The first method becomes more and more impractical as the number of reaction vessels needed increases. Regarding the second method, it is pointed out that the desired mixture would only be obtained if the rate of all 400 possible couplings were the same. A moment's reflection will serve to indicate that this is not likely to be the case. The rate of coupling of the suitably N-blocked activated carboxyl form of alanine with a resin derivatized with alanine is, indeed, not the same as the rate of reaction of N-blocked carboxy-activated proline with a resin derivatized with alanine, which is, in turn, not the same as the rate of reaction of the N-blocked carboxy-activated proline with a resin derivatized with proline.

Each of the 400 possible amino acid couplings will have its own characteristic rate constant. The problem will be aggravated upon the attempt to extend the peptide chain with the third mixture of twenty amino acids, and further complicated by extension with the fourth, etc. As more amino acids are added to the chain, the preference for the higher coupling constants is continuously tilted in favor of the faster reacting species to the near exclusion of the peptides which would result from the slower coupling constants.

The above description refers to the use of 20 different amino acyl resins in the initial mixture. These 20 resins are then reacted with 20 amino acids in order to form 400 different dipeptides. However, it is possible to use additional amino acyl resins beyond this 20 and it is possible to use substantially less. For example, the original mixture could include 10 amino acyl resins which could in turn be reacted with 10 amino acids to form 100 different dipeptides. Although larger and larger and smaller and smaller numbers can be used, the invention decreases in value as the number of peptides produced decreases. Accordingly, it is preferable to include at least 5 different amino acyl resins in the starting mixture which are to be reacted with at least 5 different amino acids in order to form 25 different dipeptides.

The large numbers of peptides are produced in accordance with the present invention by first preparing a mixture of amino acyl resins and then separating those resins into a plurality of different pools wherein each of the amino acyl resins is present in each pool in substantially equal molar amounts. Although any number of pools can be provided, 5 is generally the minimum number at which the invention shows substantial usefulness as compared with methods which simply provide for producing peptides individually. After the amino acyl resins are divided into the different pools, a different amino acid is reacted with each of the pools. The amino acid is added in an amount and under conditions so as to provide a substantially complete coupling reaction with all of the amino acyl resins in each of the pools. Accordingly, substantially equal molar amounts of each dipeptide is synthesized within each of the pools. Thereafter, the substantially equal molar amounts of dipeptides within each of the separated pools are then combined together in order to provide a mixture of peptides which contain substantially equal molar amounts of each of the dipeptides.

In accordance with the above description, if the initial mixture of amino acyl resins were divided into 20 different pools with each pool containing substantially equal molar amounts of 20 different amino acids and the 20 different pools were then each individually reacted with one different activated amino acid and the reaction were driven to completion, each pool would contain substantially equal molar amounts of 20 different peptides. The 20 different pools would then be combined to provide 400 different dipeptides. The procedure could then be repeated by (1) dividing the dipeptides into different pools and (2) carrying out reactions and then (3) recombining. It should be pointed out that the number of pools created at any given step can be varied. Accordingly, although 20 pools might be created for the first step reaction, it may be that the second amino acid in the chain is known to be one of only five known amino acids. Accordingly, an original mixture of peptides containing 20 different amino acyl resins could be divided into 5 different pools each containing equal molar amounts of the 20 amino acyl resins. The 5 pools could each then be individually reacted with one of 5 different amino acids. Each of the 5 pools would then include 20 new dipeptides. The 20 new dipeptides within each of the 5 pools could be combined together to provide 100 different dipeptides which were produced by carrying out only 5 different reactions. Accordingly, it can be seen how substantial savings in time can be obtained over prior art methods which individually produce peptides.

Isolation of full-length peptides can be further aided by utilizing a final amino acyl residue which is blocked with a selectable group such as tBOC-biotin. The use of such blocking groups is not essential for carrying out the invention. The reaction can be monitored for completion using techniques known to those skilled in the art. However, as a general principle, the use of blocking groups in order to cap the final residue is a preferred procedure in order to ensure no deletion of pepides in the final mixture. When the side chains are deprotected and peptide released from the resin, only full-length peptides will have biotin at the amino terminus, which facilitates their separation from the capped peptides. The biotinylated peptides (which are all full length due to the intermediate capping of incomplete peptides) are conveniently separated from the capped peptides by avidin affinity chromatography. Alternatively, biotin can be used to "cap" incompletely coupled peptides. Further, deletion pepides can be removed from the mixture using avidin affinity chromatography. Other specific selectable groups can be used in connection with the protecting group on the final amino acid residue to aid in separation, such as, for example, FMOC, which can also be removed.

The method of the present invention can be carried out without the need to vary the ratios and/or concentrations of activated residues in a particular mixture. Since all reactions are driven to completion it is irrelevant whether the acceptors have the same relative rates of reaction for reacting with all activated amino acids. If they do not [for example Pro has been reported to differ in relative rate from other acceptors (Kemp, D.S. et al, *J Org Chem* (1974) 39:3841–3843 (supra))], the simple approach thus far described will not be compromised because each reaction is driven to completion, eliminating the relative rate constants as a factor effecting the composition of the mixture of peptides obtained.

Selection

As described above, the method of the invention results in a complex mixture of peptides. Although the mixture is likely to be complex and contain a large number of different peptides it will have a known composition in that (i) each coupling reaction of part (2) is driven to completion; (ii) the reactants i.e., the resin and activated amino acid reacted in each pool of step (2) are known; (iii) the amount of each peptide from step (2) added in step (3) is known. Although the composition is known, only one or a few of the peptides in the mixture are desired peptides having the target property or reactivity. Accordingly, it is necessary to select from the mixture those successful products which have the required properties.

The nature of the selection process depends, of course, on the nature of the product for which selection is to be had. In a common instance, wherein the desired property is the ability to bind a protein such as an immunoglobulin, receptor, receptor-binding ligand, antigen or enzyme, selection can be conducted simply by exposing the mixture to the substance to which binding is desired. The desired peptides will bind preferentially. (Other nonprotein substances, such as carbohydrates or nucleic acids, could also be used.) The bound substances are then separated from the remainder of the mixture (for example, by using the binding substance conjugated to a solid support and separating using chromatographic techniques or by filtration or centrifugation, or separating bound and unbound peptides on the basis of size using gel filtration). The bound peptides can then be removed by denaturation of the complex, or by competition with the naturally occurring substrate which normally binds to the receptor or antibody.

This general method is also applicable to proteins responsible for gene regulation as these peptides bind specifically to certain DNA sequences.

In the alternative, peptides which are substrates for enzymes such as proteases can be separated from the remainder of the peptides on the basis of the size of cleavage products, or substrates for enzymes which add a selectable component, can be separated accordingly.

Other properties upon which separation can be based include selective membrane transport, size separation based on differential behavior due to 3-dimensional conformation (folding) and differences in other physical properties such as solubility or freezing point.

Since a number of the members of the mixture are expected to possess the desired target property to a greater or lesser degree, it may be necessary to separate further the components of the smaller mixture which has been selected by standard differentiating chromatographic techniques such as HPLC. On the other hand, it may be desirable to use the subgroup without further separation as a "family" to provide the desired activity. However, in any case, if very large subpopulations are obtained, reapplication of the selection technique at higher stringency may be needed. Analysis, as set forth below, can be conducted on individual components, or on mixtures having limited numbers of components.

Thus, for example, if a mixture of peptides binding to a given antibody or receptor contains fifty or so members, the salt concentration or pH can be adjusted to dissociate all but the most tightly binding members, or the natural substrate can be used to provide competition. This refinement will result in the recovery of a mixture with a more manageable number of components. A variety of protocols will be evident to differentiate among peptides with varying levels of the target characteristics.

Analysis

When individual peptides or manageable mixtures have been obtained, standard methods of analysis can be used to obtain the sequence information needed to specify the particular peptide recovered. These methods include determination of amino acid composition, including the use of highly sensitive methods such as fast atom bombardment mass spectrometry (FABMS) which provides the very precise molecular weight of the peptide components of the mixture and thus permits the determination of precise amino acid composition. Additional sequence information may be necessary to specify the precise sequence of the protein, however. In any event, current technology for sequence analysis permits determination on about 100 picomoles of peptide or less. A variety of analytical techniques are known in the art, and useful in the invention, as described below:

It should be emphasized that certain of these methods can be applied directly to mixtures having limited numbers of components, and the sequence of each component deduced. This application is made without prior separation of the individual components.

The ultimate success of the method in most cases depends on sequence analysis and, in some cases, quantitation of the individual peptides in the selected mixture. Techniques which are current state-of-art methodologies can be applied individually on pure components but also may be used in combination as screens. A combination of diode array detection Liquid Chromatography (DAD-LC), mixture peptide sequencing, mass spectrometry and amino acid analysis is used. To the knowledge of the present inventors, these standard methods are used for the first time in combination directly on the peptide mixtures to aid in the analysis. The following paragraphs briefly describe these techniques.

HPLC with single wavelength detection provides a rapid estimation of the complexity of a mixture and gives a very approximate estimation of the amounts of its components. This information is contained within the more precise information obtained in DAD-LC.

DAD-LC provides complete, multiple spectra for each HPLC peak, which, by comparison, can provide indication of peak purity. These data can also assign the presence of Tyr, Trp, Phe, and possibly others and can quantitate these amino acids by 2nd derivative or multi-component analysis. By a derivatization, DAD-LC can also identify and quantitate Cys, His and Arg in individual peptides. Thus, it is possible to analyze for 6 of the 20 amino acids of each separated peptide in a single LC run, and information can be obtained about the presence or absence of these amino acids in a given peptide in a single step. This is assisted by knowing the number of residues in each peptide, as is the case when carrying out the process step of the present invention. Also, by correction at 205 nm absorbance for side-chain chromophores, this technique can give much better estimation of relative amounts of each peptide.

Mass spectrometry identifies molecules according to mass and can identify peptides with unique composition, but does not distinguish isomeric sequences (tandem mass spectrometry potentially could distinguish between isomers). In effect, this method provides similar results as the amino acid analysis (AAA) of isolated peptides; the advantage is that it can be performed on mixtures in a single experiment. The disadvantage is that when applied to mixtures it is often difficult to tell which peptide belongs to which LC peak and provide quantitation (in theory this could be done by LC-mass spectrometry); further, some peptides may go undetected. For the present purpose, it is useful in conjunction with one of the other methods.

Mixture peptide sequencing is most useful for identification, especially if the selected peptides are limited in number. As sequence cycles are performed through positions where multiple amino acids were placed, the peptides show multiple derivatized amino acids present in rough proportion to their amount in the selected peptide. Quantitation of the amino acids in the different cycles can be carried out. If amino acids are present in the same sequence, they should appear in nearly identical amounts as in the sequencing cycles. When two or more selected peptides are present in similar amounts, they may be readily distinguishable by combined use of other methods mentioned. As a final resort, group separations or reactions may be performed so that sequencing will provide a unique solution.

HPLC separation and amino acid analysis or sequencing of components could also be performed. Amino acid analysis provides information on the composition, but not the specific sequence. Isolated peptides can be sequenced to give the exact identity of the solutions. Isolation is more tedious than analysis of mixes, and not doable for very large mixtures; these methods however, are quite practical for a limited number of peptides.

SUMMARY

A controlled synthesis of a mixture of peptides having a known composition and containing one or more peptides of a desired amino acid sequence is disclosed. The method involves three essential steps. First, a given amount of amino acyl resin (preferably a mixture of resins) is divided into a number of pools with each pool preferably containing an equal molar amount of resin. Second, a single amino acid is coupled to the resin in each of the pools and the coupling reaction is driven to completion. The newly created peptides (in known amounts which are preferably equal molar) in each of the pools are then mixed together to obtain a peptide mixture of known composition. The steps can be repeated to lengthen the peptide chain and chains can be linked. Thereafter, methods can be employed to retrieve the desired peptide from the mixture and carry out analyses such as the determination of the amino acid sequence.

This invention provides a simple method of preparation of complex mixtures of peptides. Because the mixture will contain detectable and retrievable amounts of desired peptides, selection of those members having the desired properties, and, if desired, analysis of those chosen few so as to permit large-scale synthesis of the desired peptides is possible. Because the mixture will contain detectable and retrievable amounts of a desired peptide or peptides, it permits selection of one or more peptides from the mixture which are superior in their properties in binding to various moieties including proteins, such as enzymes, receptors, receptor-binding ligands or antibodies, nucleic acids, and carbohydrates, reaction with enzymes to form distinct products, or other properties such as transport through membranes, anti-freeze properties, and as vaccines. In general, although short-cut methods which presuppose some features of the sequence are also available, the method, in principle, offers the opportunity to maximize the desired property without preconceived ideas as to the most successful sequence. Accordingly, the less that is known of the amino acid sequence of a protein of known properties, the more useful the present invention will be as compared with other methods.

While the present invention has been described with reference to the specific embodiments thereof, it should be understood by those skilled in the art of synthesizing peptides that various changes may be made and equivalents may be substituted without departing from the true spirit and scope of the present method for making peptide mixtures and isolating desired peptides therefrom. In addition, many modifications may be made to adapt to a particular situation, material, composition of matter, process, process step or steps, to the objective, spirit and scope of the present invention. All such modifications are intended to be within the scope of the appended claims.

We claim:

1. A method of preparing a mixture of peptides having different amino acid sequences, which mixture contains retrievable and analyzable amounts of each peptide, comprising:
    (a) dividing an amount of a mixture of amino acyl or peptide derivatized resins into a plurality of subamounts;
    (b) coupling a different single amino acid with each of the subamounts of resin to obtain a plurality of different peptide resins the coupling being carried out under conditions such that it is driven to substantial completion with each subamount; and
    (c) combining known amounts of the different peptide resins together to obtain the mixture of peptides; which mixture contains retrievable and analyzable amounts of each of the peptide resins.

2. The method as claimed in claim 1, wherein the amount of mixture in step (a) includes at least 5 different amino acyl or peptide derivatized resins in substantially equal molar amounts.

3. The method as claimed in claim 2, wherein the amount of mixture in step (a) is divided into at least 5 subamounts and wherein each of the subamounts is coupled in step (b) with a different single amino acid to obtain at least 5 different peptides in each subamount which are then combined in step (c) to obtain at least 25 different peptides, each present in retrievable and analyzable amounts.

4. The method as claimed in claim 1, wherein the amount of mixture in step (a) includes at least 10 different amino acyl or peptide derivatized resins which amount is divided into at least 10 subamounts.

5. The method as claimed in claim 4, wherein the 10 subamounts are each reacted with a different single amino acid in order to obtain at least 10 different peptides in each subamount and adding together the peptides from each subamount in step (c) in order to obtain at least 100 peptides, each present in retrievable and analyzable amounts.

6. The method as claimed in claim 1, wherein the amount of mixture in step (a) includes 20 amino acyl or peptide derivatized resins and the amount is divided into 20 subamounts with each subamount being reacted with a different single amino acid in step (b) in order to obtain 20 peptides in each of the subamounts which are then combined in step (c) to obtain a mixture of 400 peptides, each present in retrievable and analyzable amounts.

7. The method of preparing a mixture of peptides as claimed in claim 1, further comprising:
    monitoring the coupling (b) by an analytical method to determine the degree of completion of the coupling.

8. The method of preparing a mixture of peptides as claimed in claim 7, wherein the analytical method includes the use of triketohydrine hydrate.

9. The method of preparing a mixture of peptides as claimed in claim 1, further comprising:
    repeating the steps (a), (b) and (c) to increase the size of the peptides and the number of different peptides in the mixture.

10. The method of preparing a mixture of peptides as claimed in claim 9, further comprising:
    retrieving at least one peptide from the mixture having a selected target property.

11. The method of preparing a mixture of peptides as claimed in claim 10, further comprising:

analyzing the peptide having the selected target property in order to determine its amino acid sequence.

12. The method of preparing a mixture of peptides as claimed in claim 9 wherein the combining is carried out using a mixture of acceptor amino acids or peptides derivatized to a solid support through their carboxy terminus.

13. The method as claimed in claim 10, wherein the target property is binding specifically to a peptide or protein.

14. The method as claimed in claim 10, wherein the protein is selected from an immunoglobin, a receptor, an enzyme, an antigen, and a receptor-binding ligand.

15. The method as claimed in claim 10, wherein the target property is binding specifically to DNA or RNA.

16. The method as claimed in claim 10, wherein the target property is binding to a carbohydrate or glycoprotein.

17. The method as claimed in claim 10, wherein the target property is transport or passage through a membrane.

18. The method as claimed in claim 10, wherein the target property is retention by a membrane.

19. The method as claimed in claim 10, wherein the target property is utilization as a substrate or inhibitor for a designated enzyme.

20. The method as claimed in claim 10, wherein the target property is a specified set of physical characteristics.

21. The method as claimed in claim 20, wherein the set of physical characteristics includes one or more characteristics selected from freezing point, molecular size, and solubility profile.

22. A method of preparing a mixture of peptides which mixture contains substantially equal molar amounts of a plurality of different known peptides, comprising:
  (a) providing a plurality of pools each containing a mixture of amino acyl or peptide derivatized resins, each of which is present in substantially equal molar amounts;
  (b) adding a different amino acid to each of the pools, the amino acid being added in an amount and under conditions so as to provide a substantially complete coupling reaction with all the resins in each pool to obtain different peptides in substantially equal molar amounts in each pool; and
  (c) combining substantially equal molar (amounts of different peptides together to obtain a mixture of peptides which mixture contains substantially equal molar amounts of the different peptides.

23. The method of preparing a mixture of peptides as claimed in claim 22, further comprising:
  monitoring the coupling reaction in step (b) by an analytical method to determine the degree of completion of the coupling.

24. The method of preparing a mixture of peptides as claimed in claim 23, wherein the analytical method includes the use of triketohydrine hydrate.

25. The method of preparing a mixture of peptides as claimed in claim 22, further comprising:
  repeating the steps (a), (b) and (c) to increase the size of the peptides and the number of different peptides in the mixture.

* * * * *

UNITED STATES PATENT AND TRADEMARK OFFICE
CERTIFICATE OF CORRECTION

PATENT NO.   : 5,182,366

DATED        : January 26, 1993

INVENTOR(S)  : Verena D. Huebner et al.

It is certified that error appears in the above-identified patent and that said Letters Patent is hereby corrected as shown below:

In claim 14:

In column 17, line 12, delete "10" and insert --13--.

Signed and Sealed this

Fifth Day of September, 1995

Attest:

BRUCE LEHMAN

*Attesting Officer*     *Commissioner of Patents and Trademarks*